United States Patent
Moosheimer et al.

(10) Patent No.: US 8,182,450 B2
(45) Date of Patent: May 22, 2012

(54) LABEL, SYRINGE BODY AND SYRINGE ARRANGEMENT WITH LABEL

(75) Inventors: Ulrich Moosheimer, Hohenkammern (DE); Peter Seidl, Munich (DE)

(73) Assignee: Schreiner Group GmbH & Co. KG (DE)

( * ) Notice: Subject to any disclaimer, the term of this patent is extended or adjusted under 35 U.S.C. 154(b) by 783 days.

(21) Appl. No.: 12/102,792

(22) Filed: Apr. 14, 2008

(65) Prior Publication Data

US 2008/0195078 A1    Aug. 14, 2008

Related U.S. Application Data

(62) Division of application No. 10/990,750, filed on Nov. 18, 2004, now abandoned.

(30) Foreign Application Priority Data

Nov. 26, 2003  (EP) .................................. 03104390
Apr. 22, 2004  (EP) .................................. 04101672

(51) Int. Cl.
  *A61M 3/00*   (2006.01)
  *A61M 5/00*   (2006.01)
  *B32B 9/00*   (2006.01)
(52) U.S. Cl. ...... 604/189; 604/187; 428/40.1; 428/41.8; 428/42.1; 428/42.2; 428/42.3
(58) Field of Classification Search ............... 428/40.1, 428/41.8, 42.1, 42.2, 42.3; 604/187, 189
See application file for complete search history.

(56) References Cited

U.S. PATENT DOCUMENTS

| 4,312,523 | A |   | 1/1982  | Haines |
| 5,692,640 | A |   | 12/1997 | Caulfield et al. |
| 5,984,901 | A | * | 11/1999 | Sudo et al. ............... 604/227 |
| 6,030,366 | A | * | 2/2000  | Mitchell ................... 604/192 |
| 6,193,279 | B1 |  | 2/2001  | Seidl |
| 6,228,451 | B1 |  | 5/2001  | Boudouris et al. |
| 6,332,631 | B1 |  | 12/2001 | Kirk |
| 2003/0012913 | A1 | | 1/2003 | Seidl |

FOREIGN PATENT DOCUMENTS

| EP | 0463193 | 1/1992 |
| EP | 0935968 | 8/1999 |
| EP | 1044698 | 10/2000 |
| JP | 2003-512650 | 4/2003 |

* cited by examiner

*Primary Examiner* — Victor Chang
(74) *Attorney, Agent, or Firm* — Studebaker & Brackett PC; Donald R. Studebaker

(57) ABSTRACT

The label is executed as strip-shaped and adhered as directed in a self-overlapping fashion to a syringe body (1) which is inserted in a syringe protector formed from an insert (5) and a receiver (4). In the longitudinal direction of the strip it successively has a base section (11), two voucher sections (12a, 12b), a protective section (13), a holding section (14) and a grip tab (15). The label can be unrolled and pulled out from the syringe protector by a grip tab (15) so that the voucher sections (12a, 12b) are freely accessible. If necessary, after inserting the syringe body (1) into the syringe protector, the grip tab (15) can be extracted through lateral openings (24, 25) to a certain extent by gently turning the syringe body (1) relative to the syringe protector and then gripped since the grip tab (15) is at some distance after sticking the label onto the syringe body (1). If the grip tab (15) is provided with a suitable slope, during insertion of the labelled syringe body (1) into the narrow syringe protector, there is no risk of the label being kinked or otherwise damaged from its free end since the grip tab (15) lies on the labelled syringe body (1) during the insertion process.

2 Claims, 4 Drawing Sheets

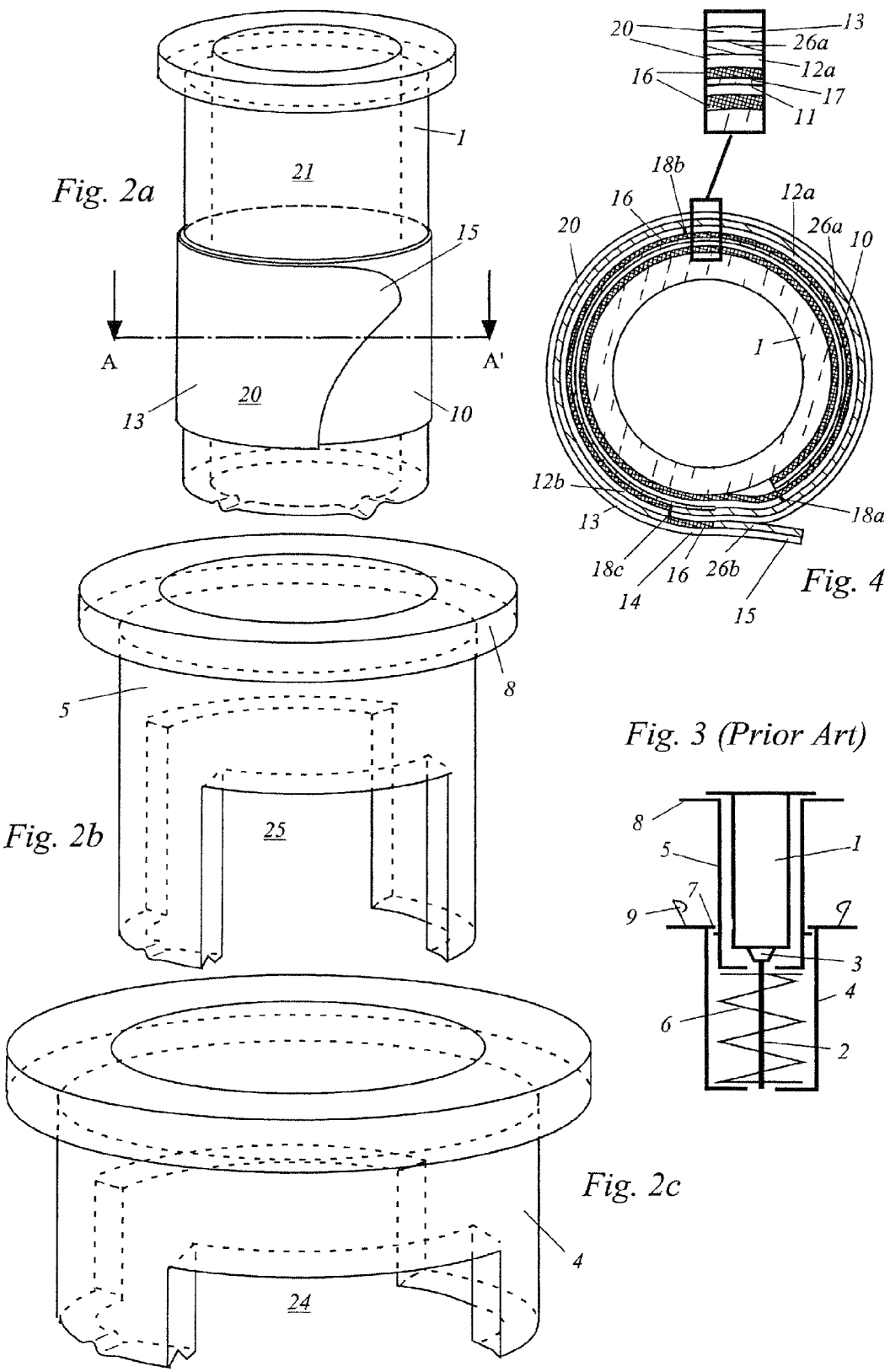

LABEL, SYRINGE BODY AND SYRINGE ARRANGEMENT WITH LABEL

This application is a divisional application of application Ser. No. 10/990,750 filed Nov. 18, 2004, now abandoned.

The present invention relates to a strip-shaped label, especially a label for wrap-around labelling of a syringe body or other container, a syringe body which has such a label and a syringe arrangement with a syringe body labelled in this fashion.

Labels of the type specified initially are frequently shaped such that their extension in the longitudinal direction of the strip is greater than the diameter of the syringe body or other container and consequently, they are stuck on in a self-overlapping fashion. A corresponding shaping is especially selected if, as a result of their small size, the syringes, ampoules and phials for pharmaceuticals would otherwise offer too little outer surface to accommodate all the information required to characterise the content on a non-overlapping label.

The space requirement increases if the label is fitted with so-called voucher sections. These are understood as regions which can be separated from the rest of the label which carry some on the label information (which is usually printed again on the part of the label left on the container) and can be stuck separately onto a documentation sheet or the like. They can be used for example to record which dose of which medicament a patient has received in which order. Such a label is known for example from EP 0 463 193 A1.

If syringe bodies, which are understood as the part of the syringe containing the injectate onto which a cannula is pushed on or screwed on, are fitted with self-overlapping labels containing voucher sections, a special handling problem frequently arises, which results from the use of so-called syringe protectors.

Syringe protectors are used to preserve a syringe before use so that on the one hand, there is protection against injury from the tip of the cannula and on the other hand, the cannula itself is protected against breaking or bending. The basic structure of a syringe arrangement with syringe protector is explained briefly in the following with reference to the schematic sectional view shown in FIG. 3.

The syringe body 1 onto which the cannula 2 is pushed or screwed by means of a connecting piece 3, is inserted in a syringe protector which substantially consists of a receiver 4 and insert 5. The insert 5 which holds the syringe body 1 is guided into the receiver 4 in the fashion of two hollow bodies placed inside one another. A pre-stressed spring 6 holds the insert 5 in an end position pre-determined by a stop 7 (hereinafter "protected position") so that the cannula 2 projecting from the insert 5 is located inside the receiver 4 over its full length. Before using the syringe the insert 5 is pressed downwards against the spring force of the spring 6 and the edge 8 of the insert 5 engages into the holders 9. Versions without engagements also exist. In this position (hereinafter "injection position") the cannula projects from the receiver 4 and the injection can be given. If the cannula 2 is protected with a solid protective cap before use, which is frequently the case in practice, the arrangement can be in the injection position from the start. In any case, the syringe protector offers protection from injury after using the syringe if the insert 5 disengages from the holders 9 and is guided backed into the protected position by the spring 6.

The problem with using syringe bodies fitted with self-overlapping labels containing voucher sections is that the voucher sections cannot be removed as long as this is inserted in the syringe protector. On the other hand, previous removal of the syringe body from the syringe protector is not provided, this would be complicated and there would be the risk of injury from the cannula tip, especially in haste.

It is thus the object of the present invention to provide a label with voucher sections which is better suited for overlapping labelling of syringe bodies inserted in syringe protectors than labels according to the prior art. It is further the object of the present invention to provide a corresponding syringe body and a syringe arrangement comprising a syringe protector which allows the removal of a voucher section labelled on the syringe body without the need to remove the syringe body from the syringe protector. The handling should be as reliable and convenient as possible.

More generally, the object of the invention is to make it possible to label a first body inserted in a second body with a label having a voucher section so that the voucher sections are removable without the need to remove the first body from the second body.

According to one aspect of the invention, this object is solved by a strip-shaped label for labelling, preferably for wrap-around labelling of a syringe body or other body according to claim 1. Preferred embodiments of the label according to the invention can be configured according to one of claims 2-23.

According to a further aspect of the invention, the object is solved by a syringe body according to claim 24. Preferred embodiments of the syringe body according to the invention can be configured according to claims 25-29.

According to a further aspect of the invention, the object is solved by an arrangement according to claim 30, which can be executed according to an advantageous embodiment according to claim 31.

If the label is stuck onto the syringe body in a self-overlapping fashion as intended, the non-adhesive grip tab is located at the free end. The grip tab must have sufficient area so that it can project through a lateral opening of the syringe protector without detaching the label and can easily be grasped. For this purpose it is advantageous if the greatest extension of the grip tab in the longitudinal direction of the strip is at least 1 mm, especially advantageously at least 2.5 mm.

If necessary, after inserting the syringe body into the syringe protector, the grip tab can be extracted to a certain extent through the lateral opening of the same by gently turning the syringe body relative to the syringe protector and then it can be grasped since the grip tab is some distance away after sticking the label onto a syringe body. In particular, if the grip tab is provided with a suitable slope or rounding, in a completely surprising fashion for the person skilled in the art, during insertion of the labelled syringe body into the narrow syringe protector the label nevertheless does not run the risk of becoming kinked or otherwise damaged from its free end since especially as a result of its preferred shaping, the grip tab lies on the labelled syringe body during the insertion process. For this purpose, the label should preferably be stuck on so that the extension of the grip tab in the longitudinal direction of the strip increases continuously from the label edge lying at the front in the direction of insertion and ideally over most of the width of the label strip. The risk of damage to the label from its free end is the lowest when the extension of the grip tab in the longitudinal direction of the strip on the label edge lying at the front in the direction of insertion is less than 10 percent of its greatest extension in the longitudinal direction of the strip. Ideally, the grip tab widens slowly over the strip width, beginning from a negligible extension in the longitudinal direction of the strip.

When the labelled syringe body is inserted in the syringe protector, the label can be partly unrolled from the syringe body by pulling on the grip tab. In this case, the label is pulled through openings in the insert of the syringe protector (in the protected position) or through openings in the insert and receiver of the syringe protector (in the injection position) until the voucher section or voucher sections can be torn off along the separating lines. Thus, it is not necessary to remove the syringe body from the syringe protector in order to reach the voucher sections. The latter can thus be removed reliably, simply, quickly, conveniently and with little expenditure.

According to a further aspect of the invention, a method is provided for documenting a product usage according to claim 32 in which, as described above, for example, the administration of an injection is involved. The separated voucher section can be stuck on a documentation record.

Exemplary examples according to the invention are described in more detail in the following with reference to the relevant drawings. The drawings are not to scale and should be understood as purely schematic. In particular, the layer thicknesses of the various label layers are greatly exaggerated for reasons of clarity. Reference numbers of corresponding features are retained throughout for all figures.

FIG. 1 shows a perspective view of a label according to the invention with two voucher sections, which is arranged on a piece of pull-off material, wherein the length-to-width ratio of the label strip is shown distorted (shortened strip length);

FIG. 2a-c shows the upper region of a syringe body labelled according to the invention and the insert and the receiver of a syringe arrangement according to the invention, in each case greatly enlarged;

FIG. 3 shows the fundamental interaction of a syringe protector with a syringe according to the prior art which equally applies to the syringe arrangement according to the invention;

FIG. 4 shows a sectional view through the syringe body from FIG. 2a in the sectional plane perpendicular to the longitudinal axis of the syringe body indicated by the line A-A' from FIG. 2a as well as an enlarged view of a section indicated by two connected rectangles;

Figure 9:
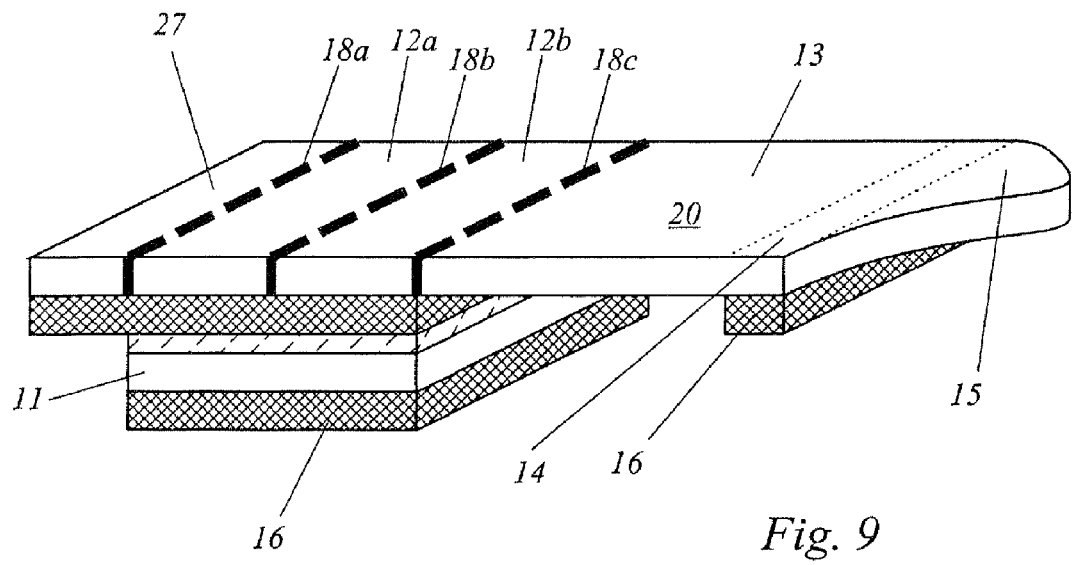
Figure 10:
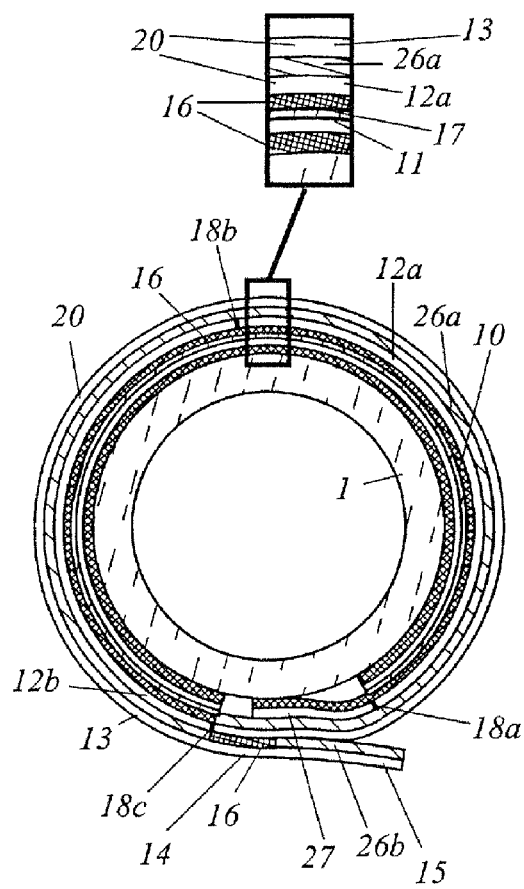

FIG. 8a-e show six different variants of the shaping of the grip tab of a label according to the invention;

FIG. 9 shows a perspective view of a further label according to the invention with two voucher sections, wherein the length-to-width ratio of the label strip is shown distorted (shortened strip length);

FIG. 10 shows a sectional view similar to FIG. 4 through a labelled syringe body in the sectional plane perpendicular to the longitudinal axis of the syringe body as well as an enlarged view of a section indicated by two connected rectangles, wherein the label is shaped similar to the embodiment from FIG. 9.

Figure 1:
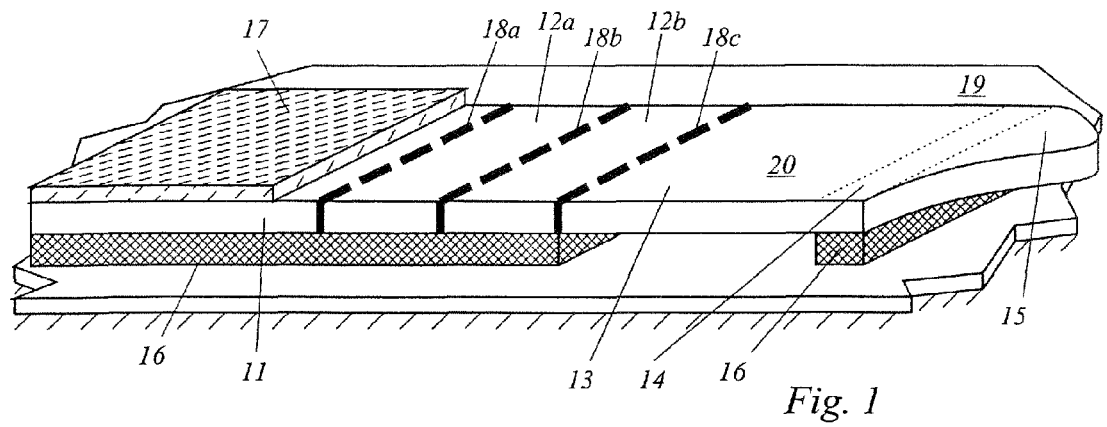

The label shown in FIG. 1 is executed in a strip shape. In the longitudinal direction of the strip (from left to right in the selected diagram) it successively has a base section 11, two voucher sections 12a, 12b, a protective section 13, a holding section 14 and a grip tab 15. Said regions 11, 12a, 12b, 13, 14, 15 are advantageously substantially formed by a continuous plastic film layer 20 which can be transparent or opaque. It is also possible to manufacture the label on a paper basis or as a multilayer foil composite. The finely dotted lines separating the holding section 14 from the protective section 13 or the grip tab 15 are for clarity and do not represent any physical feature of the invention.

For reasons of clarity the diagram is distorted such that the strip width is exaggerated in relation to the strip length and the thickness of the individual layers is shown as highly exaggerated in relation to the remaining dimensions.

On the underside the label is provided with an adhering adhesive layer 16 which is respectively interrupted in the area of the protective section 13 and the grip tab 15. Alternatively the entire underside of the label can be adhesive-coated, wherein the adhesive coating is neutralised in the area of the protective section 13 and the grip tab 15 by means of a so-called "adhesive killer", i.e., is transferred to a non-adhesive state.

The base section 11 is provided with an adhesive-repelling coating 17 (for example, a silicone layer) on the upper side which has at least the same areal extension as the entirety of the voucher sections 12a, 12b. In some cases, it can also be advantageous however if the extension of the adhesive-repelling coating is somewhat smaller so that small areas (compared with the silicone coated region) of increased adhesion provide for good cohesion before the detachment of the voucher sections.

The voucher sections 12a, 12b can be separated from the base section 11 or from one another or from the protective section 13 along the separating lines 18a, 18b, 18c which extend in the transverse direction of the strip over the total width of the label. The separating lines 18a, 18b, 18c can be executed as perforations, punching or other local weakenings of the foil layer 20 which facilitate tearing off.

The protective section 13 is wider than the entirety of the voucher sections 12a, 12b in the longitudinal direction of the strip. The holding section 14 is narrower than the remaining sections 11, 12a, 12b, 13 in the longitudinal direction of the strip. The grip tab 15 becomes continuously broader in the longitudinal direction of the strip over most of the width of the label strip. This wing-like shape of the grip tab 15 ensures that after labelling a syringe body 1 according to the invention, during insertion of the syringe body 1 into a narrow syringe protector said tab lies on the labelled syringe body as described in detail below. The decisive factor in this case is that the label is attached so that the front label edge in FIG. 1, i.e., the edge of the label 10 running in the longitudinal direction of the strip, from which the grip tab 15 becomes continuously broader over the centre (in the transverse direction of the strip) of the label, is the leading edge during insertion of the syringe body 1 into the syringe protector. In connection with the present invention, a continuous broadening from the edge over the centre (in the transverse direction of the strip) of the label is regarded as equivalent to a broadening over most of the width of the label strip. Various alternative shapes of the grip tab 15 which satisfy this criterion are shown in FIG. 8a-8e.

The label is usually printed with text and/or picture information (not shown). In the area of the base section 11 such printing is normally executed underneath the adhesive-repelling coating 17 for reasons of printing technique. The information on the first voucher section 12a is usually substantially identical to the information on the second voucher section 12b and corresponds to the information on the base section 11 so that the voucher sections 12a, 12b can (also subsequently) be assigned to one another and to the labelled syringe body 1. The information on the protective section 13 will usually mostly correspond to the information on the base section 11 since after labelling the syringe body 1 initially only the former and not the latter can be seen, as is explained below. The printed information can among other things comprise active substance, information on quantity and concentration, shelf life data, batch numbers, barcodes, trade and producer marks etc. Furthermore, areal printing can also be provided as colour background, especially when the plastic film layer 20 is executed as transparent.

Over the adhering adhesive layer 16 the label is arranged on a piece of pull-off material 19 shown in part, from which it can easily be detached to be stuck onto the syringe body 1 as intended.

FIG. 2a shows a syringe body 1 on which a label is stuck, which is constructed substantially as the label shown in FIG. 1. For reasons of clarity the syringe body 1 is shown greatly enlarged, like the insert shown in FIG. 2b and the receiver shown in FIG. 2a, and specifically in relation to the size of the label 10 which usually covers most of the outer surface 21 of the syringe body 1 in actual application.

A plane of intersection perpendicular to the longitudinal axis of the syringe body 1 is indicated by the dot-and-dash line A-A'. A corresponding sectional view (in the direction of the arrow) is shown in FIG. 4 with greatly exaggerated layer thicknesses of the layers 16, 17, 20 and 26 of the label 10 in relation to FIG. 2a. A further enlargement of a section is illustrated by the two rectangles outlined in bold in the upper part of FIG. 4 where the upper of the two rectangles shows an enlarged view of the same section as the lower one.

The label overlaps itself twice. In this case, in the area of the voucher sections 12a, 12b the adhering adhesive layer 16 lies on the adhesive-repelling coating 17 of the base section 11 which for its part is stuck onto the outer surface 21 of the syringe body 1. The protective section 13 covers the voucher sections 12a, 12b. Unlike FIG. 1, the non-adhesive underside of the protective section 13 and the grip tab 15 are not achieved by an interruption of the adhering adhesive layer 16 but by the adhering adhesive layer 16 being neutralised in the corresponding areas 26a, 26b by using a so-called "adhesive killer", i.e., being converted to a non-adhesive state.

The holding section 14 sticks over a narrow non-neutralised region of the adhering adhesive layer 16 on an area of the protective section 13 adjacent to the voucher section 12b in order to hold together the overlapping arrangement of the label and secure it against unintentional unrolling.

Both the syringe body 1 in FIG. 2a and also the insert 5 in FIG. 2b and the receiver 4 in FIG. 2c which represent parts of the syringe protector of the syringe arrangement according to the invention are only shown in part, i.e., they are shown as broken off downwards. The insert 5 is guided into the receiver 4, as shown in FIG. 3. Otherwise, the basic principle of the interaction between syringe body 1, insert 5 and receiver 4 of the syringe arrangement according to the invention is fundamentally the same as that described in the prior art and above with reference to FIG. 3. Mechanical details already known from the prior art such as the stop 7 and the holders 9 are also not shown in FIG. 2b and FIG. 2c for the sake of simplicity.

The receiver 4 and insert 5 preferably consist of transparent plastic so that the imprint (not shown) on the protective section 13 stays legible when the labelled syringe body 1 is inserted into the insert 5. The openings 24, 25 are used to make it possible to have access to the grip tab 15 even when the labelled syringe body 1 is inserted into the insert 5 and the syringe protector substantially consisting of receiver 4 and insert 5 is located in the injection position. Accordingly, access to the grip tab 15 is only possible through the opening 25 of the insert 5 when the syringe protector is in the protected position.

The labelled syringe body 1 is inserted into the insert 5 from above. In this case, as a result of its shaping according to the invention, the grip tab 15 which is normally slightly at a distance because of its non-adhesive underside as shown in FIG. 4, lies on the protective section 13. It is thus prevented that during insertion of the labelled syringe body 1 into the insert 5 the holding region 14 detaches and crumples the label, as would be the case if the free end of the label was less favourably shaped.

Figure 5:
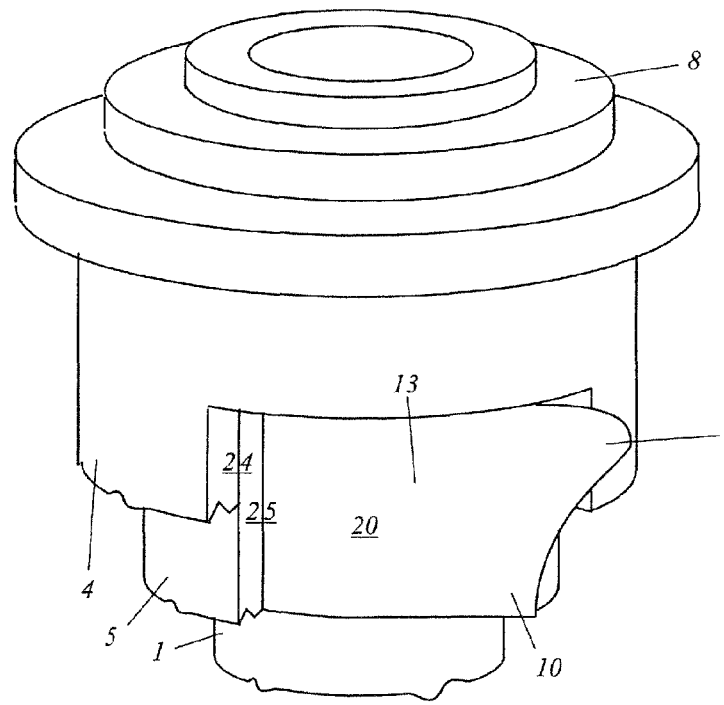
FIG. 5 shows the parts of the syringe arrangement shown in FIGS. 2a-c, inserted inside one another wherein the tab already projects somewhat from the lateral opening of the receiver (transparency of the parts of the syringe arrangement is not taken into account in the diagram)
Figure 6:
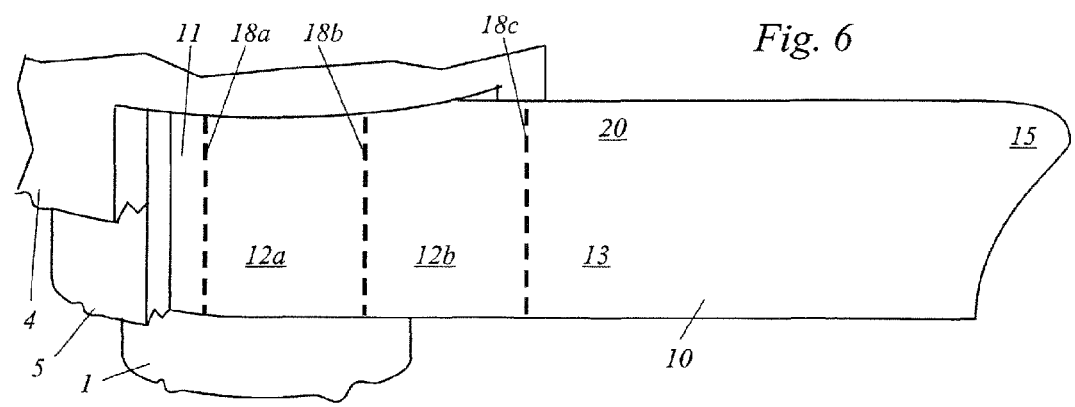
FIG. 6 shows a section of the syringe arrangement from FIG. 5 wherein the label is pulled out further so that both voucher sections are visible.

FIGS. 5 and 6 show the syringe arrangement according to the invention in part with the syringe body 1 already inserted into the injection position. The transparency of the components is not indicated graphically for the sake of clarity.

In FIG. 5 the grip tab 15 already projects somewhat through the openings 24, 25 from the syringe protector formed from the insert 5 and receiver 4 so that it can easily be grasped. This state can easily be brought about in the winding of the label shown in the anticlockwise direction by turning the labelled syringe body 1 slightly in the anticlockwise direction relative to the insert 5 and receiver 4.

FIG. 6 shows the state after pulling on the grip tab 15. The label is now further unwound and pulled further from the syringe protector formed by the insert 5 and receiver 4 so that the voucher section 12b is already freely accessible. By further pulling on the grip tab 15, the other voucher section 12a also becomes freely accessible.

Figure 7:
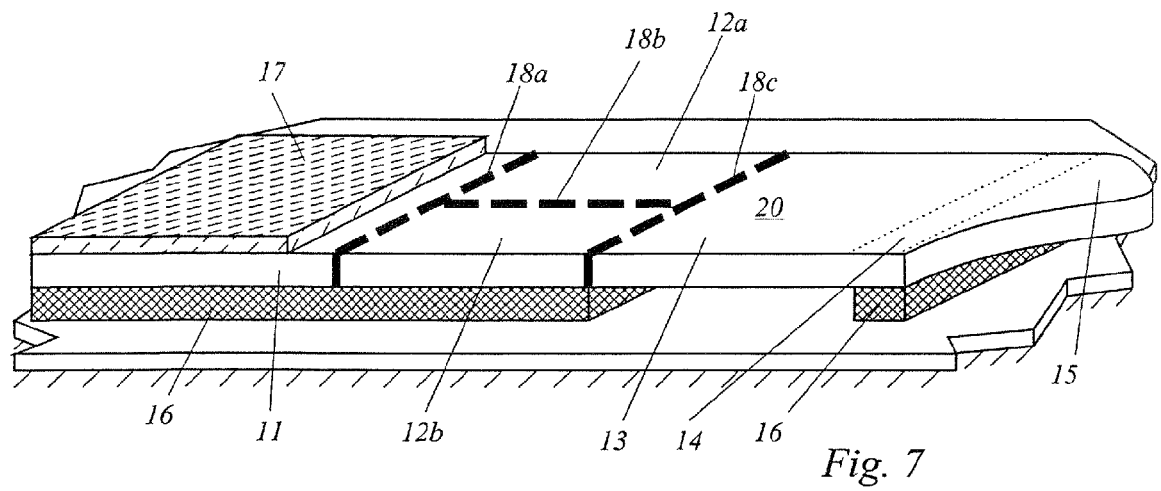
FIG. 7 shows a label which differs from the label shown in FIG. 1 by an alternative arrangement of the voucher sections.
Figure 8A:
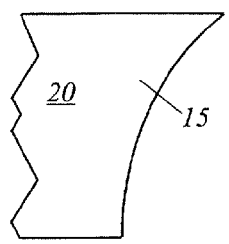
Figure 8B:
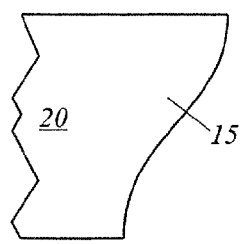
Figure 8C:
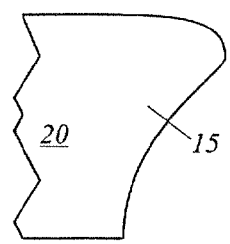
Figure 8D:
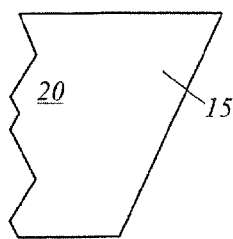
Figure 8E:
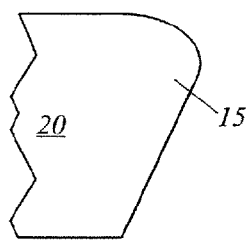
Figure 8F:
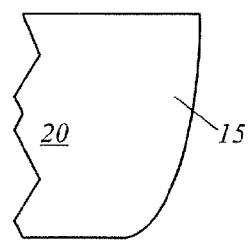

FIG. 7 shows an alternative arrangement of the voucher sections 12a, 12b. The diagram substantially corresponds to FIG. 1. The separating lines 18a, 18c which run over the entire width of the label in the transverse direction of the strip make it possible to separate the voucher sections 12a, 12b from the base section 11 or the protective section 13. The voucher sections 12a, 12b can be separated from one another via the separating line 18b running in the longitudinal direction of the strip. In addition, other arrangements of one, two or more voucher sections are also possible.

Like the label shown in FIG. 1, the label shown in FIG. 9 is also executed as strip-shaped. For reasons of clarity the diagram is distorted such that the strip width is exaggerated in relation to the strip length, and the thickness of the individual layers is shown greatly exaggerated in relation to the other dimensions.

In the longitudinal direction of the strip (from left to right in the selected diagram) the label successively has an initial section 27, two voucher sections 12a, 12b, a protective section 13, a holding section 14 and a grip tab 15. Said regions 27, 12a, 12b, 13, 14 and 15 are advantageously substantially formed from a continuous layer of plastic film 20 which can be transparent or opaque. Likewise, it is also possible to manufacture the layer on a paper basis or as a multilayer foil composite. The finely dotted lines separating the holding section 14 from the protective section 13 or the grip tab 15 are for clarity and do not represent any physical feature of the invention.

The label shown in FIG. 9 differs from the embodiment shown in FIG. 1 in that the base section 11 is arranged below and not next to the voucher sections 12a, 12b. In contrast to the label from FIG. 1 which can be manufactured from a single foil blank, in the case of the label shown in FIG. 9, the base section 11 and the entirety of the remaining sections 12a, 12b, 13, 14, 15 are each made from their own foil blank. The foil blank adhesive-coated on the underside forming the regions 12a, 12b, 13, 14, 15 is dispensed on the base section 11 having an adhesive-repellent coating on the upper side, which is arranged on a piece of pull-off material, which is not shown in FIG. 9 in contrast to FIG. 1.

On the underside each foil blank of the label is provided with an adhering adhesive layer 16 which is interrupted respectively in the area of the protective section 13 and the grip tab 15. Alternatively the entire underside of the label can be adhesive-coated wherein the adhesive coating is neutralised with a so-called "adhesive killer" in the area of the protective section 13 and the grip tab 15, i.e., is converted to a non-adhesive state.

In the present exemplary embodiment the base section 11 is provided on the upper side with an adhesive-repellent coating 17 (for example, a silicone layer) which has at least the same areal extension as the entirety of the voucher sections 12a, 12b. In other cases, it can also be advantageous if the extension of the adhesive-repellent coating is somewhat smaller so that small areas (compared with the siliconeised area) of elevated adhesion provide good cohesion before the voucher sections are detached.

The voucher sections 12a, 12b can be separated from the initial section 11 or from one another or from the protective section 13 along the separating lines 18a, 18b, 18c which extend in the transverse direction of the strip over the entire width of the label. The separating lines 18a, 18b, 18c can be executed as perforations, punching or other local weakenings of the foil layer 20 which facilitate tearing off.

The protective section 13 is wider than the entirety of the voucher sections 12a, 12b in the longitudinal direction of the strip. The holding section 14 is narrower than the sections 11, 12a, 12b, 13 in the longitudinal direction of the strip. The grip tab 15 becomes continuously broader in the longitudinal direction of the strip over most of the width of the label strip. This wing-like shape of the grip tab 15 ensures that after labelling a syringe body 1 according to the invention, during insertion of the syringe body 1 into a narrow syringe protector said tab lies on the labelled syringe body as described in detail below. The decisive factor in this case is that the label is attached so that the front label edge in FIG. 1, i.e., the edge of the label 10 running in the longitudinal direction of the strip, from which the grip tab 15 becomes continuously broader over the centre (in the transverse direction of the strip) of the label, is the leading edge during insertion of the syringe body 1 into the syringe protector. Various alternative shapes of the grip tab 15 which satisfy this criterion are shown in FIG. 8a-8e.

The label is usually printed with text and/or picture information (not shown). In the area of the base section 11 such printing is normally executed underneath the adhesive-repelling coating 17 for reasons of printing technique. The information on the first voucher section 12a is usually substantially identical to the information on the second voucher section 12b and corresponds to the information on the base section 11 so that the voucher sections 12a, 12b can (also subsequently) be assigned to one another and to the labelled syringe body 1. The information on the protective section 13 will usually mostly correspond to the information on the base section 11 since after labelling the syringe body 1 initially only the former and not the latter can be seen, as is explained below. The printed information can among other things comprise active substance, information on quantity and concentration, shelf life data, batch numbers, barcodes, trade and producer marks etc. Furthermore, areal printing can also be provided as colour background, especially when the plastic film layer 20 is executed as transparent.

The initial section 27 is generally significantly shorter than the base section 11. Preferably it is shorter than one fifth of the base section 11 or shorter than one tenth of the circumference of the area of the intended syringe body 1 to be labelled. The initial section 27 improves the dispensability of the label but can frequently be superfluous however.

Compared to the embodiment shown in FIG. 1, the label from FIG. 9 has the advantage that the label strip is shorter overall whereby the label can be applied more simply and more quickly to the syringe body 1 especially in the case of mechanical dispensing. It is further possible to make the base section 11 and the remaining sections 27, 12a, 12b, 13, 14, 15 from different foil materials whereby, in addition to other feasible advantages, under certain circumstances the total thickness of the label layers wound onto the syringe body 1 as intended can be somewhat thinner. On the other hand, the expenditure for manufacturing the label from FIG. 1 is lower than that for manufacturing the label from FIG. 9.

By analogy with FIG. 4, FIG. 10 shows a sectional view of a labelled syringe body 1. The label applied thereto in a self-overlapping fashion is executed substantially as the label shown in FIG. 9. An enlarged section is illustrated, as in FIG. 4, by the two rectangles outlined in bold in the upper section of FIG. 10 where the upper of the two rectangles shows the same section enlarged as the lower rectangle.

In the area of the voucher sections 12a, 12b the adhering adhesive layer 16 lies on the adhesive-repelling coating 17 of the base section 11 which for its part is stuck onto the outer surface 21 of the syringe body 1. The protective section 13 covers the voucher sections 12a, 12b as a result of the overlapping application. Unlike FIG. 9, the non-adhesive underside of the protective section 13 and the grip tab 15 are not achieved by an interruption of the adhering adhesive layer 16 but by the adhering adhesive layer 16 being neutralised in the corresponding areas 26a, 26b by using a so-called "adhesive killer", i.e., being converted to a non-adhesive state.

The holding section 14 sticks over a narrow non-neutralised region of the adhering adhesive layer 16 on an area of the protective section 13 adjacent to the voucher section 12b in order to hold together the overlapping arrangement of the label and secure it against unintentional unrolling.

For better fixing of the voucher sections 12a, 12b and to facilitate the labelling, especially when mechanical dispensing is used, the initial section 27 adheres directly on the syringe body 1.

From a comparison of FIG. 4 and FIG. 10 it can be seen that when the labels are applied as intended, the two arrangements of the label layers on the labelled syringe body 1 barely differ from one another despite the labels being executed differently (compare FIGS. 1 and 9). Both syringe bodies 1 can be inserted in the same way into the insert 5 of a syringe protector and offer substantially the same functionality.

The invention claimed is:

1. A syringe arrangement having an outer body with a lateral opening wherein the outer body is a syringe protector with a receiver having at least one lateral opening and an insert having at least one further lateral opening, and an inner body inserted in the outer body, the inner body is a syringe body, wherein the inner body has adhered thereto a strip-shaped label such that a longitudinal direction of the strip corresponds to a circumferential direction of the inner body, said label having the following sections beside one another in the longitudinal direction of the strip:
  at least one voucher section which can be separated from the remaining label in the longitudinal direction of the strip along at least one separating line running in the transverse direction of the strip and which has an adhesive coating on its underside at least over part of the area,
  a grip tab which is not adhesive on the underside and which is arranged, in the longitudinal direction of the strip, terminally on the label, wherein at least one of the separating lines is arranged between the grip tab and each voucher section, said label having furthermore a base section which on the upper side has an adhesive-repelling surface at least over part of the area and on the underside has an adhesive coating at least over part of the area, said syringe body being rotatably arranged within the outer body such that the syringe body is turnable in relation to the receiver and the insert, the lateral opening of the receiver and the lateral opening of the insert are formed so that the label can be unrolled partly from the syringe body by pulling on the grip tab through the lateral openings of the insert and the receiver and can be pulled out of the syringe protector so that the voucher sections can be separated without the need to remove the syringe body from the syringe protector.

2. The arrangement according to claim 1, implemented as a syringe arrangement, wherein the label can be unrolled partly from the syringe body by pulling on the grip tab through the lateral openings of the insert and the receiver and can be pulled out of the syringe protector so that the voucher section can be separated without the need to remove the syringe body from the syringe protector.

* * * * *